(12) United States Patent
Bhattacharya et al.

(10) Patent No.: US 12,049,663 B2
(45) Date of Patent: Jul. 30, 2024

(54) METHODS OF DETERMINING DNA BARCODES FOR EFFICIENT SPECIES CATEGORIZATION USING NANOPORE TRANSLOCATION

(71) Applicant: University of Central Florida Research Foundation, Inc., Orlando, FL (US)

(72) Inventors: Aniket Bhattacharya, Orlando, FL (US); Swarnadeep Seth, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 292 days.

(21) Appl. No.: 17/649,577

(22) Filed: Feb. 1, 2022

(65) Prior Publication Data

US 2022/0243253 A1 Aug. 4, 2022

Related U.S. Application Data

(60) Provisional application No. 63/199,898, filed on Feb. 1, 2021.

(51) Int. Cl.
*C12Q 1/68* (2018.01)
*G06F 17/18* (2006.01)

(52) U.S. Cl.
CPC ............... *C12Q 1/68* (2013.01); *G06F 17/18* (2013.01)

(58) Field of Classification Search
None
See application file for complete search history.

(56) References Cited

PUBLICATIONS

Pud et al., Mechanical Trapping of DNA in a Double-Nanopore System. Nano Lett. 2016. vol. 16: 8021-2082.
Sakaue. Nonequilibrium dynamics of polymer translocation and straightening. Phys. Rev. E. 2007. vol. 76: 021803.
Ikonen et al., Influence of non-universal effects on dynamical scaling in driven polymer translocation. J. Chem. Phys. 2012. vol. 137: 085101.
Bhattacharya and Seth. Tug of war in a double-nanopore system. Phys. Rev. E. 2020. vol. 101: 052407.
Seth and Bhattacharya. Polymer escape through a three dimensional double-nanopore system. J. Chem. Phys. 2020. vol. 153: 104901.

*Primary Examiner* — G. Steven Vanni
(74) *Attorney, Agent, or Firm* — Owen G. Behrens; Smith & Hopen, P.A.

(57) ABSTRACT

Methods of accurately determining DNA barcodes using a cylindrical nanopore system. The methods include steps of leveraging the average velocity of a double-stranded DNA segment passing through a single cylindrical nanopore that is measured through repeated scanning to accurately determine protein tag locations on the double-stranded DNA segment. As such, the methods provide for the accurate calculation of a barcode for the double-stranded DNA segment based on protein tag locations without underestimation or overestimate issues. The underlying concept and the methods are equally applicable to other multi-nanopore systems which use the dwell time and time of flight velocities to measure the barcodes.

20 Claims, 9 Drawing Sheets

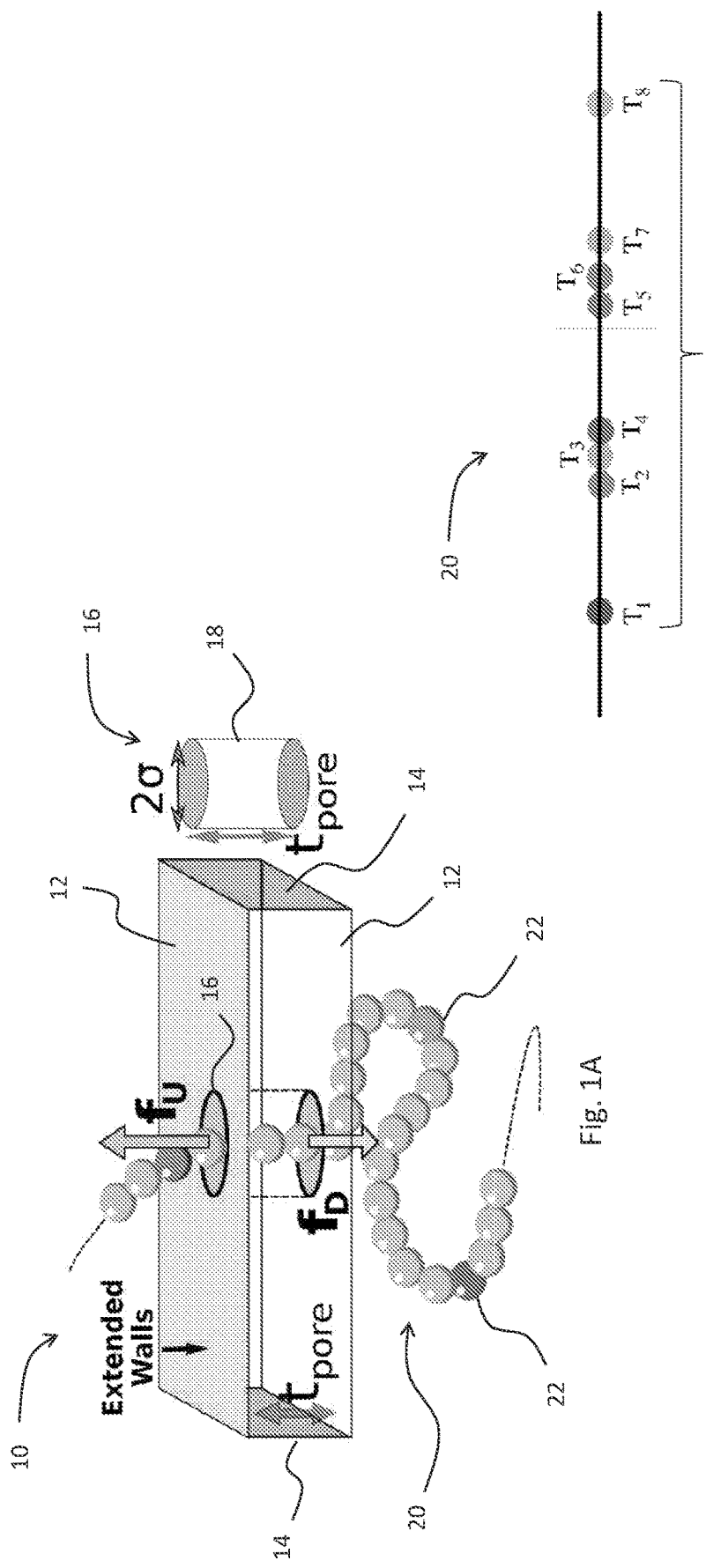

METHODS OF DETERMINING DNA BARCODES FOR EFFICIENT SPECIES CATEGORIZATION USING NANOPORE TRANSLOCATION

CROSS-REFERENCE TO RELATED APPLICATIONS

This application claims priority to provisional application No. 63/199,898, entitled "Methods of determining DNA barcodes for efficient species categorization using nanopore translocation," filed on Feb. 1, 2021 by the same inventors, the entirety of which is incorporated herein by reference.

BACKGROUND OF THE INVENTION

1. Field of the Invention

This invention relates, generally, to methods of species categorization. More specifically, it relates to methods of determining DNA barcodes for efficient species categorization without relying on traditional chemical-based DNA sequencing of lengthy sections of nucleotides.

2. Brief Description of the Prior Art

The methods of DNA sequencing and species categorization provide essential insight into basic biological research for studied species, and help describe relationships between different species. The knowledge gained through DNA sequencing techniques is useful across a broad scientific spectrum, such as by conserving biodiversity [1], estimating phyletic diversity, identifying disease vectors [2], authenticating herbal products [3], unambiguously labeling food products [4, 5], and protecting endangered species [1]. Rather than sequencing an entire DNA strand, researchers determined that DNA barcodes could be determined based on a targeted gene, and that these barcodes yield accurate species identifications. A DNA barcode consists of a short strand of DNA sequence taken from a targeted gene like COI or cox I gene (Cytochrome C Oxidase 1) [6] present in the mitochondrial gene in animals. As such, during the early $21^{st}$ century, DNA sequencing techniques dramatically improved as quicker categorizations were possible based on these DNA barcodes.

To determine the DNA barcode, traditional sequencing methods based on chemical analyses are widely used in the biological community. Recently, nanopore-based sequencing methods [7] have been explored in a dual nanopore system for a cost effective, high throughput, chemical-free, and real time barcode generation. Dual nanopore systems determine DNA barcodes by scanning a captured dsDNA (double stranded DNA) multiple times as the strand passes through both pores of the dual nanopore system, applying a net periodic bias across the two pores. However, such a system relies on the accurate calculation of dwell time or time of flight (TOF) of the barcodes (tags) using the current blockage information from individual nanopores. As the tags are heavier and bulkier in nature, they produce significant current blockage (increased dwell time) compared to the normal nucleotide monomers. The disparate velocity of tags and monomers within a segment leads to an over/underestimation of the distance between sequential tags if only dwell or TOF velocity information is used.

Accordingly, what is needed is an improved method of DNA barcoding to efficiently categorize species without suffering from over/underestimation problems related to the distance between measured tags within the DNA sequence. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a method of categorizing a species associated with a segment of double-stranded DNA is now met by a new, useful, and nonobvious invention.

The novel method includes a step of passing a segment of double-stranded DNA through a singular cylindrical nanopore formed within a test chamber. The segment of double-stranded DNA includes a plurality of monomers, a first protein tag, and a subsequent protein tag. Each of the plurality of monomers and each protein tag have an equal size, shape, and volume. In an embodiment, the test chamber includes two opposing longitudinal walls joined together by two opposing lateral walls, such that the singular cylindrical nanopore is formed between the two opposing longitudinal walls, such that a central axis of the singular cylindrical nanopore is parallel to each of the two opposing lateral walls. In an embodiment, the singular cylindrical nanopore has an associated diameter of $2\sigma$, where $\sigma$ is a diameter of each of the plurality of monomers, the first protein tag, and the subsequent protein tag.

The method includes a step of calculating an average scanning velocity of the segment of double-stranded DNA by dividing a length of the segment of double-stranded DNA by an average scanning time for the double-stranded DNA taken for multiple scans. In an embodiment, the method includes a step of retaining at least a portion of the segment of double-stranded DNA within the singular cylindrical nanopore throughout each of the multiple scans. In an embodiment, the method includes a step of passing the segment of double-stranded DNA through the singular cylindrical nanopore in an opposing direction and repeating the steps of calculating the average scanning velocity, calculating the estimated distance between the first protein tag and the subsequent protein tag, calculating the estimated number of monomers of the plurality of monomers, calculating the weighted velocity of the segment of double-stranded DNA, and calculating the distance between the first protein tag and the subsequent protein tag. A bias voltage is applied to the test chamber in a reverse direction prior to passing the segment of double-stranded DNA through the singular cylindrical nanopore in the opposing direction.

An estimated distance between a first protein tag and a subsequent protein tag of the segment of double-stranded DNA is calculated by measuring, for the first protein tag and the subsequent protein tag, a dwell time and a dwell velocity based on an entry time into the singular cylindrical nanopore and an exit time from the singular cylindrical nanopore. Using the estimated distance between the first protein tag and the subsequent protein tag, an estimated number of monomers of the plurality of monomers that are disposed between the first protein tag and the subsequent protein tag is calculated.

A weighted velocity of the segment of double-stranded DNA is calculated using the dwell velocity for each of the first protein tag and the subsequent protein tag, the average scanning velocity of the segment of double-stranded DNA, and the estimated number of monomers. In an embodiment, the weighted velocity of the segment of double-stranded DNA is calculated using $$v_{weight}^{U \to D} = \frac{1}{N_{mn}}[v_{dwell}^{U \to D}(m) + v_{dwell}^{U \to D}(n) + (N_{mn} - 2)\bar{v}_{scan}],$$

where $v_{weight}^{U \to D}$ is the weighted velocity in a downward direction through the singular cylindrical nanopore, $N_{mn}$ is the estimated number of monomers of the plurality of monomers, $v_{dwell}^{U \to D}(m)$ is the dwell velocity of the first protein tag in the downward direction through the singular cylindrical nanopore, $v_{dwell}^{U \to D}(n)$ is the dwell velocity of the subsequent protein tag in the downward direction through the singular cylindrical nanopore, and $\bar{v}_{scan}$ is the calculated average scanning velocity of the segment of double-stranded DNA. In an embodiment, the method includes a step of passing the segment of double-stranded DNA through the singular cylindrical nanopore in an opposing direction. The weighted velocity of the segment of double-stranded DNA in an upward direction through the singular cylindrical nanopore is calculated using $$v_{weight}^{U \to D} = \frac{1}{N_{mn}}[v_{dwell}^{U \to D}(m) + v_{dwell}^{U \to D}(n) + (N_{mn} - 2)\bar{v}_{scan}].$$

The method includes a step of calculating the distance between the first protein tag and the subsequent protein tag by multiplying the weighted velocity of the segment of double-stranded DNA by a time delay between the entry time of the first protein tag and the entry time of the subsequent protein tag. In an embodiment, the steps of calculating a distance between sequential protein tags is repeated for a plurality of protein tags within the segment of double-stranded DNA.

An embodiment of the novel method includes a step of applying a first voltage to a first side of a test chamber that defines a singular nanopore therethrough. Based on the applied first voltage, the method includes a step of passing the segment of double-stranded DNA through the first side of the singular nanopore defined by the test chamber. The method includes a step of applying a second voltage to a second side of the test chamber, with the second side of the test chamber being opposite the first side of the test chamber, such that a bias voltage applied to the test chamber reverses. Based on the applied second voltage, the method includes a step of passing the segment of double-stranded DNA through the second side of the singular nanopore in a direction toward the first side of the test chamber.

An embodiment of the novel method includes calculating the distance between the first protein tag and the subsequent protein tag for each of a plurality of protein tags on a segment of dsDNA. The method includes a step of generating a barcode for the segment of double-stranded DNA by arranging the plurality of protein tags of the segment of double-stranded DNA in sequential order.

An object of the invention is to provide efficient and accurate methods of calculating distances between sequential protein tags of a double-stranded DNA, thereby providing for efficient categorization of species based on the calculated DNA barcode.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 1A depicts a schematic diagram depicting a dsDNA strand being scanned through a cylindrical nanopore device translocating in the direction of the bias net force $\pm|\Delta \vec{f}_{UD}|=\pm|\vec{f}_U - \vec{f}_D|$, in accordance with an embodiment of the present invention.

FIG. 1B depicts an example of the positions of protein tags ($T_1$ through $T_8$) along the contour length of a model dsDNA, in accordance with an embodiment of the present invention.

DETAILED DESCRIPTION OF THE INVENTION

Figure 1C:
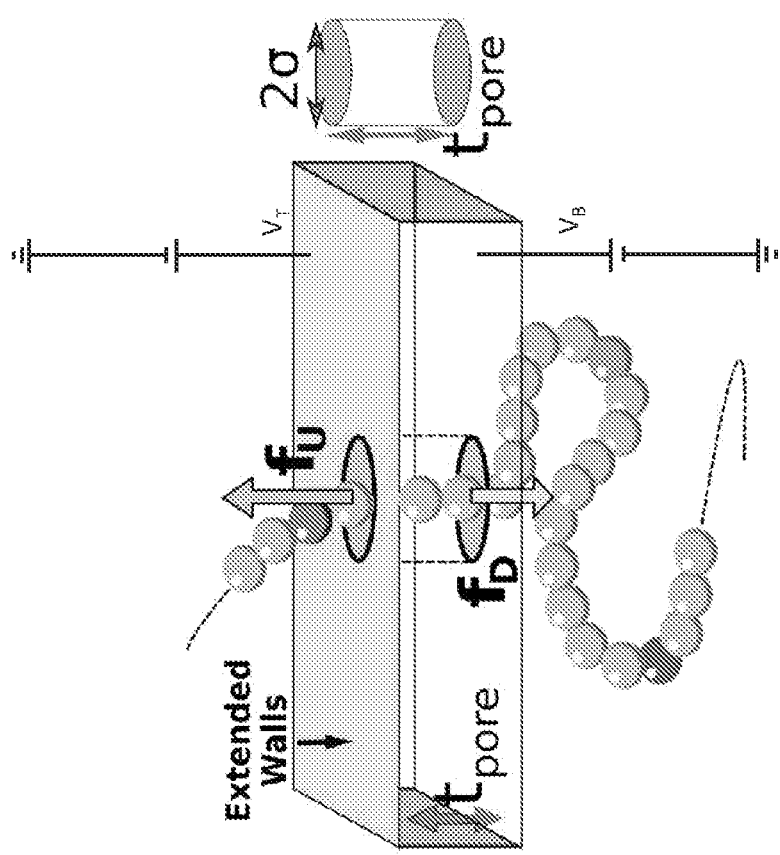
FIG. 1C depicts an electrical schematic diagram showing an applied voltage on a first side of a nanopore ($V_T$) and an applied voltage on a second side of the nanopore ($V_B$), such that a bias net force can be reversed, in accordance with an embodiment of the present invention.
Figure 2:
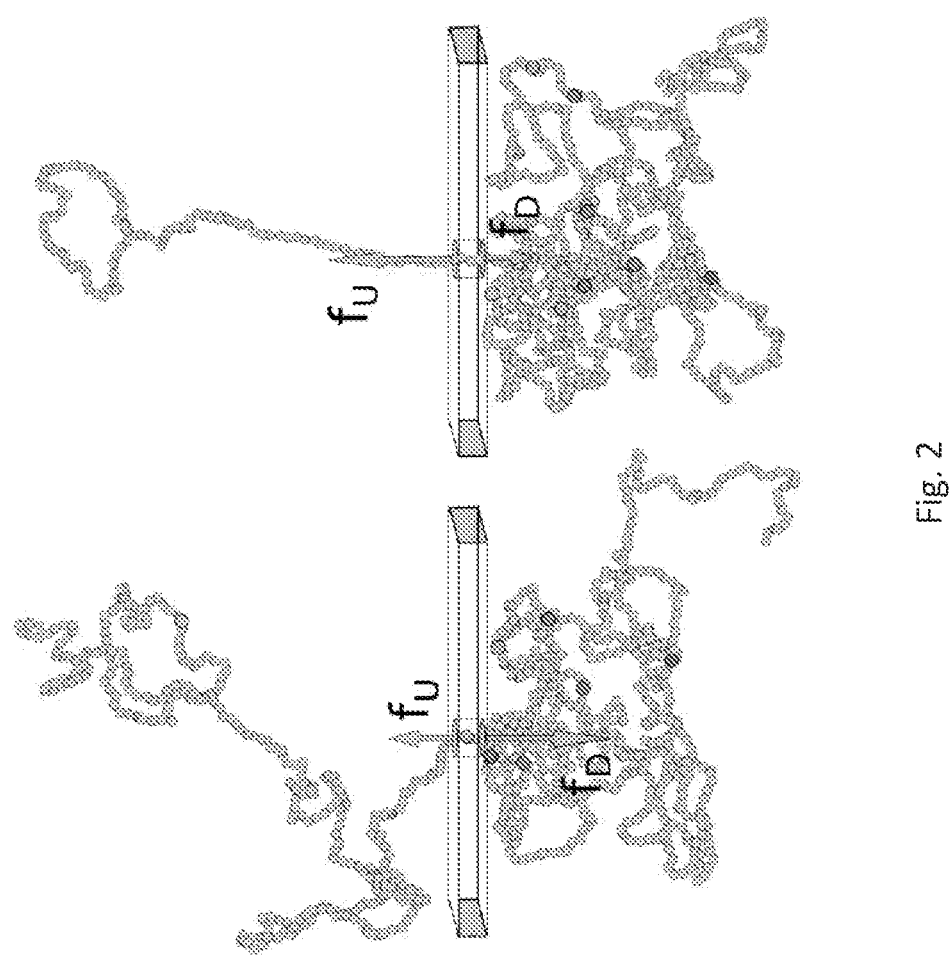
FIG. 2 depicts an embodiment of a dsDNA translocating through a cylindrical pore, showing a bias net force of $\Delta \vec{f}_{DU} = \vec{f}_D - \vec{f}_U > 0$ on the left side, and showing a bias net force of $\Delta \vec{f}_{UD} = \vec{f}_U - \vec{f}_D > 0$ on the right side, in accordance with an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes methods of accurately determining DNA barcodes using a cylindrical nanopore as opposed to a dual nanopore architecture. The methods of the present invention explain the underestimation of DNA tags caused by the fast-moving nucleotides in between the barcodes of a strand using tension propagation theory [8]. Instead, the methods described herein, schematic and graphical diagrams of which are shown in FIGS. 1A-3 and 5, leverage the average velocity of a dsDNA segment passing through a single cylindrical nanopore measured through repeated scanning to accurately determine tag locations to barcode the dsDNA segment without the underestimation issues of the prior art. These methods are described in greater detail herein below.

As shown in particular in FIG. 1A, dsDNA test chamber 10 includes a body that is defined by dual opposing longitudinal walls 12 and dual opposing lateral walls 14, with each longitudinal wall 12 secured to each lateral wall 14, such that opposing longitudinal walls 12 are spaced apart from each other, and such that opposing lateral walls 14 are spaced apart from each other. The body of dsDNA test chamber 10 defines nanopore 16, therethrough, with nanopore 16 spanning between opposing longitudinal walls 12, such that a central axis of nanopore 16 is approximately aligned with opposing lateral walls 14. As such, the body of dsDNA test chamber 10 includes one or more interior lateral walls 18 that define nanopore 16 therebetween. In an embodiment, dsDNA test chamber 10 includes a single interior lateral wall 18, such that the defined nanopore 16 is cylindrical in shape; however, it should be appreciated that in alternative embodiments, nanopore 16 may be defined as geometrical shapes including polygonal wall orientations, such as triangular, rectangular, pentagonal, hexagonal, and the like.

In addition, still referring to FIG. 1A, a diameter of the defined nanopore 16 (the distance between the one or more interior lateral walls 18) measures approximately $2\sigma$, where $\sigma$ is the diameter of each monomer or tag present on a segment of dsDNA passing through nanopore 16. In embodiments, during translocation through nanopore 16, a time is measured for the passage of each tag from a first end of nanopore 16 (defined by a first wall of opposing longitudinal walls 12) and a second end of nanopore 16 (defined by a second wall of opposing longitudinal walls 12). For example, in the embodiment shown in FIG. 1B, a plurality of tags 22 ($T_1$ through $T_8$) of dsDNA 20 are spaced apart from one another, such that a translocation time of each tag 22 can be determined during passage through nanopore 16. The time of the translocation for each tag 22 is defined as the dwell time W(m) and is used to determine a dwell velocity of each tag 22, as will be described in greater detail below.

Similar to a double nanopore setup, the single cylindrical nanopore 16 includes a periodical variation in the differential bias applied at nanopore 16 to scan the co-captured DNA multiple times. The force bias direction is altered when either of the end tags is detected at the nanopore preventing the DNA chain from escaping the nanopore for a long time. Specifically, referring to the embodiment shown in FIG. 2, as a segment of dsDNA passes through nanopore 16 in a direction with tag 22 $T_1$ passing through nanopore 16 first and tag 22 $T_8$ passing through nanopore 16 last, a downward bias net force of $\Delta \vec{f}_{DU} = \vec{f}_D - \vec{f}_U > 0$ acts on the dsDNA until tag 22 $T_8$ traverses through nanopore 16. After tag 22 $T_8$ traverses through nanopore 16 and each of the plurality of tags 22 pass through nanopore 16, a bias voltage applied to dsDNA test chamber 10 reverses such that an upward bias net force of $\Delta \vec{f}_{UD} = \vec{f}_U - \vec{f}_D > 0$ acts on the dsDNA until tag 22 $T_1$ completes a translocation through nanopore 16, at which time the bias voltage applied to dsDNA test chamber 10 reverses again (shown in detail in FIG. 1C). As such, dsDNA test chamber 10 provides for the repeated scanning of each of the plurality of tags 22 to obtain an accuracy averaged dwell time and dwell velocity for each tag 22.

As shown in FIG. 1C, an embodiment of dsDNA test chamber 10 includes a first voltage source (labeled as $V_T$) opposite a second voltage source (labeled as $V_B$). The first voltage source $V_T$ is in electrical communication with a first wall of opposing longitudinal walls 12; similarly, the second voltage source $V_B$ is in electrical communication with a second wall of opposing longitudinal walls 12. As such, the opposing voltage sources $V_T$ and $V_B$ are disposed on opposite sides of nanopore 16. As the plurality of tags 22 translocate through nanopore 16 in a direction with tag 22 $T_1$ passing through nanopore 16 first and tag 22 $T_8$ passing through nanopore 16 last, with the downward bias net force of $\Delta \vec{f}_{DU} = \vec{f}_D - \vec{f}_U > 0$ acting on the dsDNA, the applied second voltage source $V_B$ is greater than the applied first voltage source $V_T$. After tag 22 $T_8$ passed through nanopore 16, the bias voltage reverses, such that the applied first voltage source $V_T$ is greater than the applied second voltage source $V_B$. In an embodiment, a feature is added to opposing ends of a strand of dsDNA 20, such that one feature is disposed proximate to tag 22 $T_1$, with tag 22 $T_1$ being disposed between the feature and tag 22 $T_2$; similarly, the other feature is disposed proximate to tag 22 $T_8$, with tag 22 $T_8$ being disposed between the feature and tag 22 $T_7$. As such, upon the passage of one of the features through an end of nanopore 16, the bias voltage reverses, thereby allowing the reverse scanning of the strand of dsDNA 20 via a flossing technique. It should be appreciated that other methods of reversing bias voltages can be used in combination with dsDNA test chamber 10, such as utilizing field programmable gate arrays to input a control logic to automatically reverse the bias voltage and recapture scanned tags 22 by progressively increasing the number of tags 22 scanned during flossing.

Figure 3:
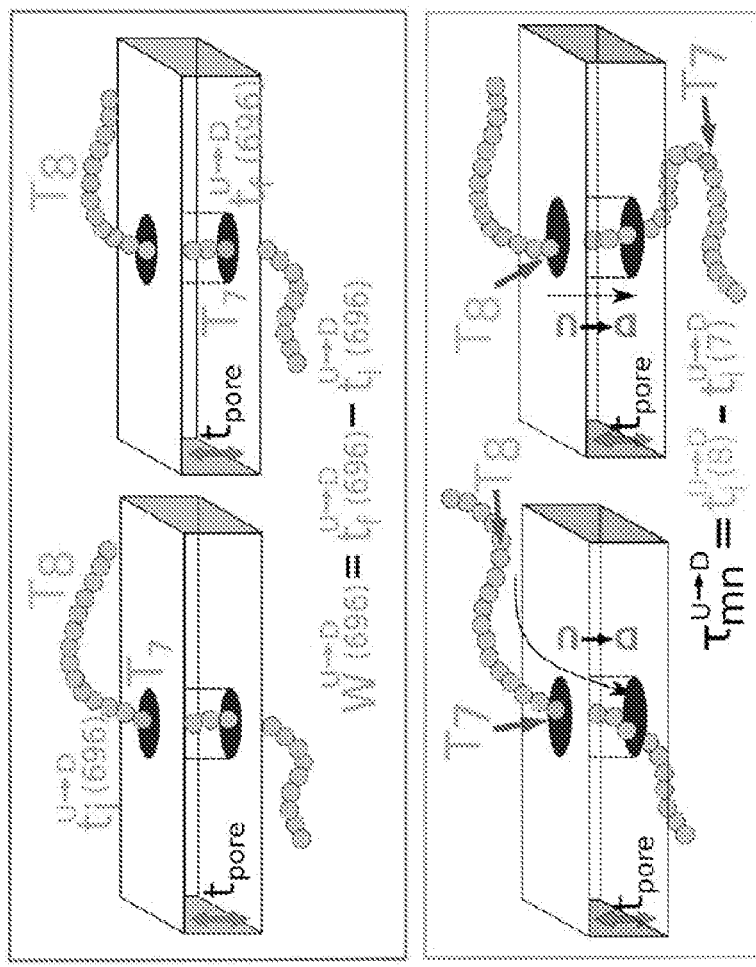
FIG. 3 depicts a graphical representation of measuring the dwell velocity and tag time delay between two tags ($T_7$ and $T_8$) using a cylindrical nanopore, in accordance with an embodiment of the present invention.

As described above, entry time $t_i$ (m) and exit time $t_f$ (m) of each tag 22 and monomer with index m is recorded as the monomer/tag passes through the nanopore 16 membrane during each scan event, resulting in a calculation of the dwell time W(m). As shown in FIG. 3, the dwell time W(m) for a monomer/tag is hereby obtained from the difference between the exit and arrival time as:

$$W^{U \to D}(m) = t_f^{U \to D}(m) - t_i^{U \to D}(m) \quad (1a)$$

$$W^{D \to U}(m) = t_f^{D \to U}(m) - t_i^{D \to U}(m) \quad (1b)$$

with $t_i^{U \to D}$ (m) and $t_f^{U \to D}$ (m) being the arrival and exit times of a monomer with index m through nanopore 16 traveling in a downward, as shown in FIG. 3 (for example, the dwell time calculation for tag 22 $T_7$ which has a monomer index m=696 is shown in detail in FIG. 3). In addition, the dwell velocities of all tags 22 $v_{dwell}$ (m) for upward and downward translocation of the dsDNA segment through nanopore 16 having a defined length along a central axis thereof (i.e., the distance between opposing longitudinal walls 12) of $t_{pore}$ are calculated based on the following dwell time information, with U→D representing the downward translation and D→U representing the upward translation:

$$v_{dwell}^{U \to D}(m) = t_{pore}/W^{U \to D}(m) \quad (2a)$$

$$v_{dwell}^{D \to U}(m) = t_{pore}/W^{D \to U}(m) \quad (2b)$$

Figure 4:
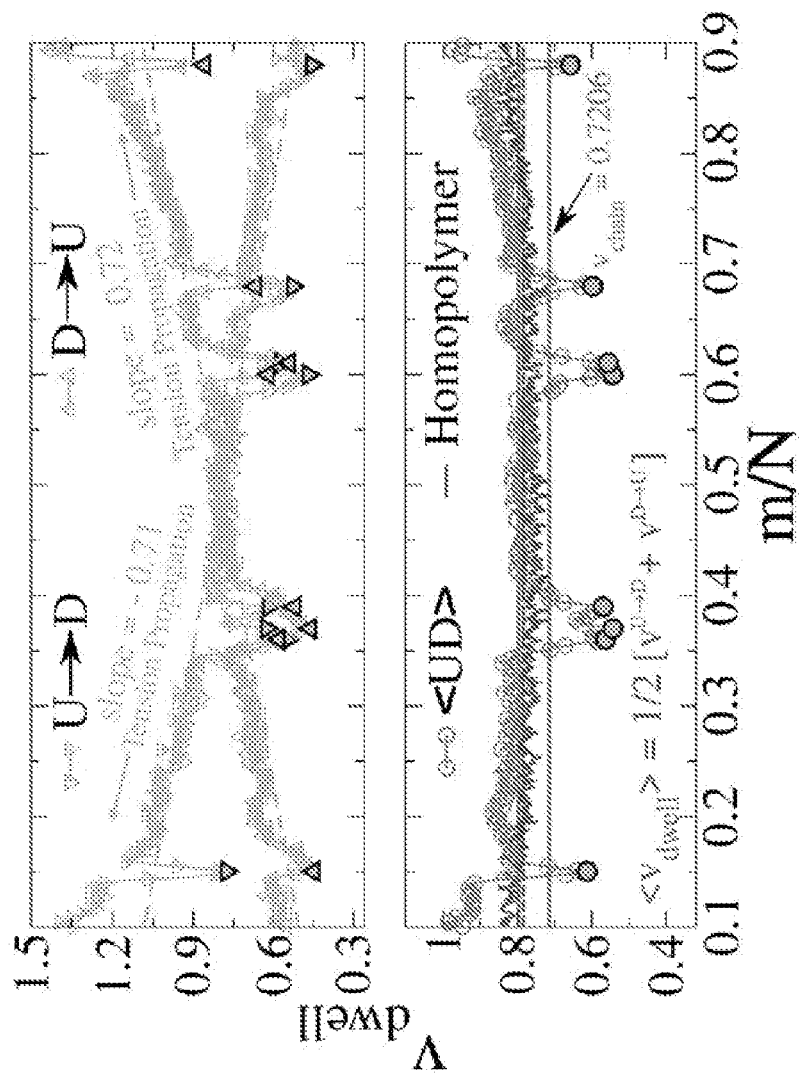
FIG. 4 depicts the dwell velocity of the monomers in a downward translocation direction U→D (downward facing triangles), in an upward translocation direction D→U (upward facing triangles), and the corresponding averaged velocities (circles), in accordance with an embodiment of the present invention.
Figure 5:
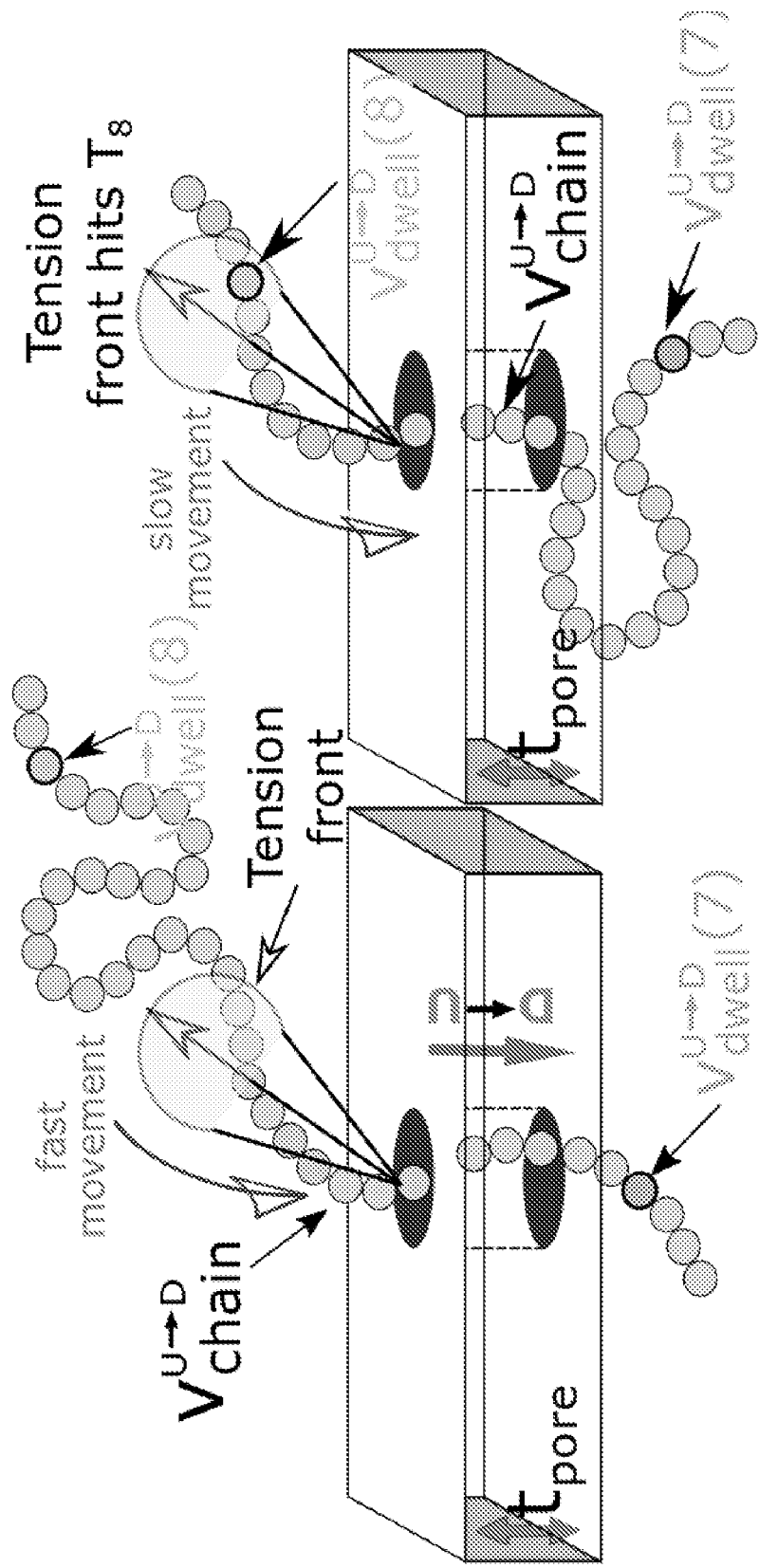
FIG. 5 depicts an example of tension propagation within a DNA strand, specifically showing the quicker passage of monomers through a pore, in accordance with an embodiment of the present invention.

The presence of tags with heavier mass ($m_{tag} > m_{bulk}$) and larger solvent friction ($\gamma_{tag} > \gamma_{bulk}$) introduces a large variation in the dwell time and, hence, a large variation in the dwell velocities of the dsDNA monomers and tags, as shown in FIG. 4 (downward triangles for downward dwell velocities, upward triangles for upward dwell velocities, and circles for averaged dwell velocities; in addition, filled triangles and circles correspond to dwell velocities for tags 22, while empty triangles and circles correspond to monomer velocities). In general, there is no up-down symmetry for the dwell time/velocity as tags 22 are not located symmetrically along the chain backbone. Thus, the physical quantities are averaged over U→D and D→U translocation data. The average dwell velocity, calculated as:

$$\bar{v}(m) = \frac{1}{2}[v_{dwell}^{U \to D}(m) + v_{dwell}^{D \to U}(m)] \quad (2c)$$

as shown in FIG. 4, which show two different velocity envelopes—the tags residing at the lower envelope.

If the dsDNA were a rigid rod, then the barcode distance ($d_{mn}^{U \to D}$) between tags $T_m$ and $T_n$ is calculated by:

$$d_{mn}^{U \to D} = v_{mn}^{U \to D} \times \tau_{mn}^{U \to D} \quad (3a)$$

$$v_{mn}^{U \to D} = \frac{1}{2}[v_{dwell}^{U \to D}(m) + v_{dwell}^{U \to D}(n)] \quad (3b)$$

$$\tau_{mn}^{U \to D} = (t_i^{U \to D}(n) - t_i^{U \to D}(m)) \quad (3c)$$

for U→D translocation; the same set of equations are derived for D→U translocation by interchanging the indices U to D and vice versa. Equations 3a-3c provide the shortest distance between the tags, but not necessarily the contour length, or the actual distance, between the tags. As such, such a calculation is likely to provide an underestimation of the barcodes.

Unlike a rigid rod, tension propagation is important in the semi-flexible dsDNA chain's motion in the presence of an external bias force, as the motion of the dsDNA subchain in the cis side decouples into two domains [8, 9]. As the dsDNA travels through the nanopore 16, after the tag 22 $T_m$ translates through the nanopore 16, the preceding monomers are quickly dragged into the nanopore 16 quickly by the tension front of the dsDNA, similar to an uncoiling effect of a rope pulled from one end. As such, faster motion occurs as the monomer strand translates through the nanopore 16, hitting a maximum at the subsequent tag 22 $T_{m \pm 1}$ with greater inertia and viscous drag. At this tension propagation time, the faster motion of the monomers (shown in FIG. 5) begins to taper down to the velocity of the tag 22 $T_{m \pm 1}$. This process continues from one segment to the other. Equations 3a-3c do not account for these contour lengths of faster moving segments in between sequential tags 22, leading to an underestimation of tags 22 and mischaracterization of the DNA barcode.

Accordingly, a first improved method for accurately determining tag 22 locations, without underestimations, includes measuring a barcode from known end-to-end tag 22 distances. By adding additional tags 22 disposed at the approximate ends of a dsDNA chain or by considering two end tags 22 ($T_1$ and $T_8$, with a distance therebetween being defined as $d_{18} \cong L$), an average velocity for the dsDNA chain is calculated by:

$$v_{chain}^{U \to D} \approx v_{18}^{U \to D} = d_{18}/\tau_{18}^{U \to D} \quad (4)$$

where $\tau_{18}^{U \to D}$ is the time delay of arrival for tags 22 $T_1$ and $T_8$ at the nanopore 16 for U→D scan direction. The barcode distance between tags 22 $T_m$ and $T_n$ is then calculated by multiplying the time delay with the $v_{18}^{U \to D}$ velocity:

$$d_{mn}^{U \to D} = v_{18}^{U \to D} \times \tau_{mn}^{U \to D} \quad (5)$$

The method is effective for estimating long-spaced barcodes; however, the method may be prone to overestimate barcode distances if multiple tags 22 are next to each other.

As such, a second improved method including a two-step process can be employed to correct for overestimations using the average scan time for the entire time, measured experimentally, to estimate the average velocity of the dsDNA chain. The scan length $L_{scan}$ is the maximum length up to which the dsDNA segment (including monomers and tags 22) remains captured inside nanopore 16 for scanning events. The scan length denotes the theoretical maximum beyond which the dsDNA will escape from the nanopore 16, $L \approx L_{scan}$. The average scanning velocity from a number of repeated scans, such as 500 independent scans, is calculated by Equation 6:

$$v_{scan} = \frac{1}{N_{scan}} \sum_i \frac{L_{scan}}{\tau_{scan}(i)} \quad (6)$$

where $\tau_{scan}$ (i) is the scan time for the $i^{th}$ event, $N_{scan}$ is the number of scanning events, and the average chain velocity is $v_{chain} \approx \bar{v}_{scan}$. Using the results from the calculations for normal monomers moving with $\bar{v}_{scan}$, while tag 22 particles each include respective dwell velocities, the segment velocity between two tags 22 is estimated by taking the weighted average of the velocities from both tags 22 and normal monomers.

During the first step of the method, the barcode distance between $T_m$ and $T_n$ is calculated using only tag velocities $v_{dwell}$ (m) and $v_{dwell}$ (n), using Equations 3a-3c. The estimated distance $d_{mn}$ is used to approximately calculate the number of monomers $N_{mn} = d_{mn}^{U \to D}/\langle b_1 \rangle$ present in a segment joining the two tags $T_m$ and $T_n$, with $\langle b_1 \rangle$ being the bond-length. In the second step, the segment velocity is re-calculated by accounting weighted velocity contribution from both tag 22 and non-tag counterpart as:

$$v_{weight}^{U \to D} = \frac{1}{N_{mn}} [v_{dwell}^{U \to D}(m) + v_{dwell}^{U \to D}(n) + (N_{mn} - 2)\bar{v}_{scan}] \quad (7)$$

The same set of equations for D→U direction is obtained by interchanging U with D. The barcodes are finally calculated by multiplying the weighted two-step velocity by the tag time delay as:

$$d_{mn}^{U \to D} = v_{weight}^{U \to D} \times \tau_{mn}^{U \to D} \quad (8)$$

The two-step method accurately captures barcode distances across the range of the dsDNA segment, independent of the proximity of the sequential tags. The underlying concept used in the single nanopore case is equally applicable to other multi-nanopore systems which use the dwell time and time of flight velocities to measure the barcodes.

Experimental Results

Figure 6A:
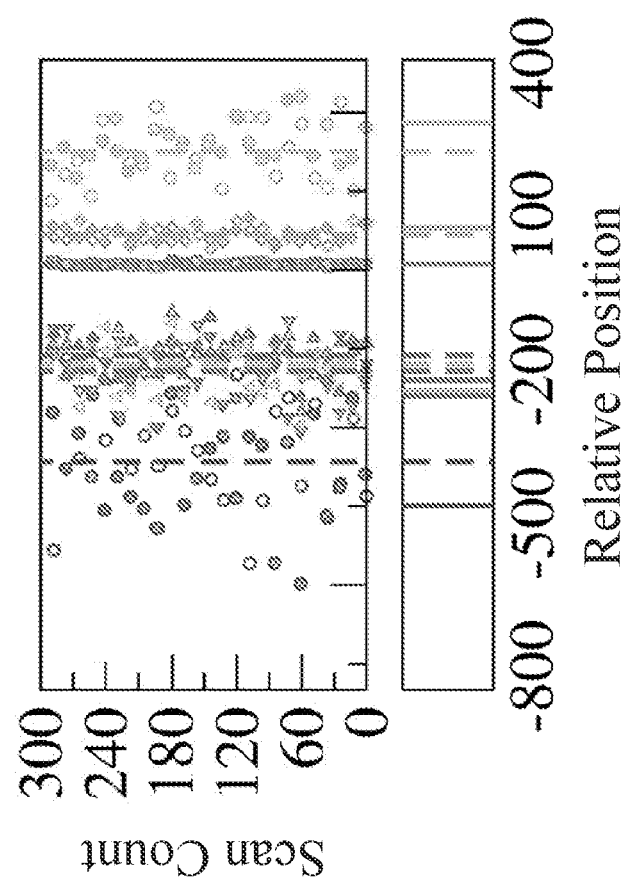
FIG. 6A depicts experimental results of a calculated DNA barcode, in accordance with an embodiment of the prevent invention.
Figure 6B:
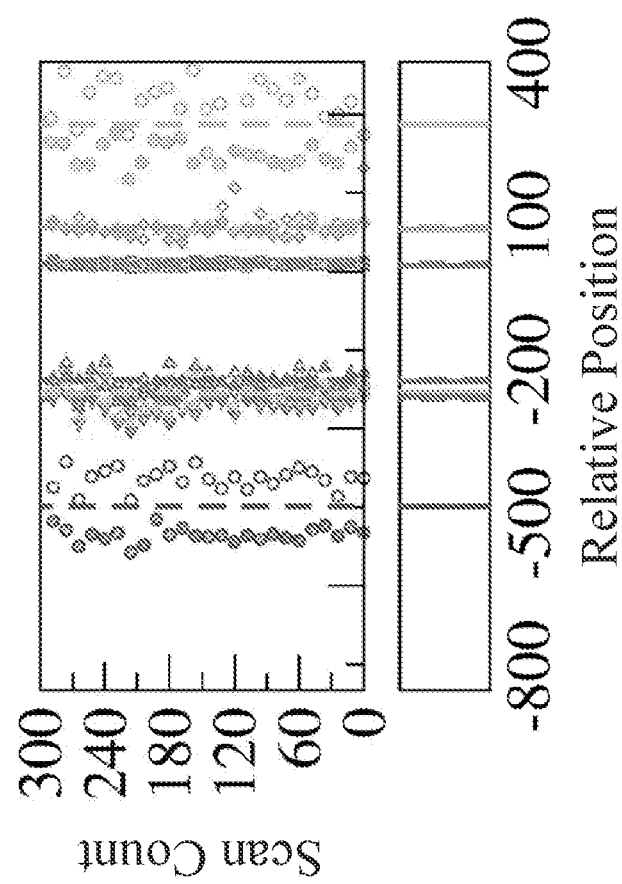
FIG. 6B depicts experimental results of a DNA barcode generated using measured dwell velocities of tags with a known end-to-end tag distance in a single nanopore device, in accordance with an embodiment of the prevent invention.
Figure 6C:
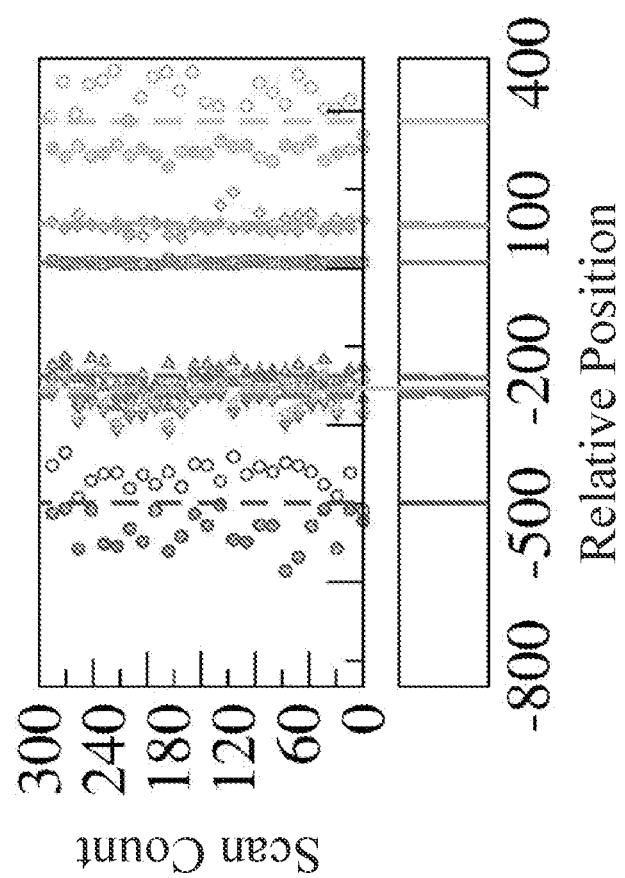
FIG. 6C depicts experimental results of a DNA barcode generated using measured dwell velocities of tags using an average scan time of an entire strand in a single nanopore device, in accordance with an embodiment of the prevent invention.

To test the methods described herein, an in silico coarse-grained (CG) model of a dsDNA segment including 1,024 monomers interspersed with 8 barcodes at different distances shown in FIG. 1, approximately mimicking previous studies on longer dsDNA segments (e.g., Zhang et al. including a dsDNA segment with 48,000 base pairs and protein tags of 75 base pairs used as barcodes) [10-12]. The positions of the 8 barcodes (as shown in Table 1) were chosen to study whether disparate distances among barcodes affects measurements and accuracies. The tags were introduced by choosing the mass and friction coefficient at tag locations that differ from that of the monomers along the dsDNA chain. The heavier and extended tags introduce a larger viscous drag as compared with the lighter monomers. Moreover, instead of explicitly putting side-chains at the tag locations, the mass and the friction coefficient of the tags were generated to be three times larger than similar measurements of the monomers, providing sufficient information to determine the distance between the tags. FIGS. 6A-6C show simulation results of barcodes generated from the dwell velocity of tags 22 in a single nanopore 16 device using: Equations 3a-3c (shown in FIG. 6A); the single-step method described in detail above (shown in FIG. 6B); and the two-step method described in detail above (shown in FIG. 6C). Furthermore, Table 2 shows the underlying data from the graphical depictions of FIGS. 6A-6C (the abbreviation w.r.t in Table 2 denotes "with respect to," such that the positions of each tag 22 in Table 22 is measured with respect to $T_5$).

TABLE 1

Tag positions along dsDNA

| Tag # | $T_1$ | $T_2$ | $T_3$ | $T_4$ | $T_5$ | $T_6$ | $T_7$ | $T_8$ |
|---|---|---|---|---|---|---|---|---|
| Position | 154 | 369 | 379 | 399 | 614 | 625 | 696 | 901 |
| Separation | 154 | 215 | 10 | 20 | 215 | 11 | 71 | 205 |

TABLE 2

Barcodes measured from different methods

| Tag # | Relative Distance w.r.t T5 | Method of Equations 3a-3c | One-Step Method | Two-Step Method |
|---|---|---|---|---|
| $T_1$ | 460 | 373 ± 122 | 459 ± 59 | 460 ± 43 |
| $T_2$ | 245 | 197 ± 67 | 250 ± 39 | 250 ± 32 |
| $T_3$ | 235 | 183 ± 63 | 237 ± 38 | 237 ± 32 |
| $T_4$ | 215 | 167 ± 54 | 211 ± 35 | 211 ± 30 |
| $T_5$ | 0 | 0 | 0 | 0 |
| $T_6$ | 11 | 11 ± 3 | 14 ± 4 | 11 ± 3 |
| $T_7$ | 82 | 68 ± 23 | 86 ± 23 | 86 ± 21 |
| $T_8$ | 287 | 230 ± 73 | 287 ± 65 | 287 ± 73 |

Conclusion

The barcode determination method described above, utilizing an in-silico Brownian dynamics scheme on a model dsDNA with known locations of the barcodes, a broad distribution of DNA tags can be accurately identified for species classification without overestimation or underestimation issues. The method includes the scanning of dsDNA through a cylindrical nanopore multiple times and uses the dwell time data of the tags in conjunction with a weighted extrapolation scheme to calculate the average velocities of the chain segment in between two tags. Using one of the tags as a reference, the barcodes are calculated multiplying time delays between sequential tags by the corresponding segment velocities using Equations 6 and 7.

REFERENCES

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

[1] R. Vernooy, E. Haribabu, M R. Muller, et al, PLoS Biol. 8(7), e1000417 (2010).

[2] N. J. Besansky, D. W. Severson, and M. T. Ferdig, Trends in Parasitology, 19, 545, (2003).

[3] N. Techen, I. Parveen, Z. Pan, and I. A Khan, Current Opinion in Biotechnology, 25, 103 (2014).

[4] X. Xiong, F. Yuan, M. Huang, L. Lu, X. Xiong, and J. Wen, J Food Prot, 82, 1200 (2019).

[5] E. H. -K. Wong, R. H. Hanner, Food Research International, 41, 828 (2008).

[6] P. D. N. Hebert, S. Ratnasingham, and J. R. de Waard, Proc R Soc Biol Sci Ser B, 270, 96 (2003).

[7] S. Pud, S. Chao, M. Belkin, D. Verschureren, T. Huijben, C. van Engelenburg, C. Dekker, and A. Aksimentiev, Nano Lett. 16, 8021 (2016).

[8] T. Sakaue, Phys. Rev. E 76, 021803 (2007).

[9] T. Ikonen, A. Bhattacharya, T. Ala-Nissila and W. Sung, J. Chem. Phys. 137, 085101 (2012).

[10] Y. Zhang, X. Liu, Y. Zhao, J. K. Yu, W. Reisner, and W. B. Dunbar, Small 14, 1801890 (2018).

[11] X. Liu, Y. Zhang, R. Nagel, W. Reisner, W. B. Dunbar, Small 15, 1901704 (2019).

[12] X. Liu, P. Zimny, Y. Zhang, A. Rana, R. Nagel, W. Reisner, and W. B. Dunbar, Small 16, 1905379 (2020).

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of calculating a distance between sequential protein tags within a segment of double-stranded DNA, the method comprising the steps of:
    passing the segment of double-stranded DNA through a singular cylindrical nanopore formed within a test chamber, the segment of double-stranded DNA including a plurality of monomers, a first protein tag, and a subsequent protein tag, each of the plurality of monomers and each protein tag having an equal size, shape, and volume;
    calculating an average scanning velocity of the segment of double-stranded DNA by dividing a length of the segment of double-stranded DNA by an average scanning time for the double-stranded DNA taken for multiple scans;
    calculating an estimated distance between a first protein tag and a subsequent protein tag of the segment of double-stranded DNA by measuring, for the first protein tag and the subsequent protein tag, a dwell time and a dwell velocity based on an entry time into the singular cylindrical nanopore and an exit time from the singular cylindrical nanopore;
    using the estimated distance between the first protein tag and the subsequent protein tag, calculating an estimated number of monomers of the plurality of monomers that are disposed between the first protein tag and the subsequent protein tag;
    calculating a weighted velocity of the segment of double-stranded DNA using the dwell velocity for each of the first protein tag and the subsequent protein tag, the average scanning velocity of the segment of double-stranded DNA, and the estimated number of monomers; and
    calculating the distance between the first protein tag and the subsequent protein tag by multiplying the weighted velocity of the segment of double-stranded DNA by a time delay between the entry time of the first protein tag and the entry time of the subsequent protein tag.

2. The method of claim 1, wherein the test chamber includes two opposing longitudinal walls joined together by two opposing lateral walls, such that the singular cylindrical nanopore is formed between the two opposing longitudinal walls, wherein a central axis of the singular cylindrical nanopore is parallel to each of the two opposing lateral walls.

3. The method of claim 1, wherein the singular cylindrical nanopore has an associated diameter of $2\sigma$, where $\sigma$ is a diameter of each of the plurality of monomers, the first protein tag, and the subsequent protein tag.

4. The method of claim 1, wherein the weighted velocity of the segment of double-stranded DNA is calculated using $$v_{weight}^{U \to D} = \frac{1}{N_{mn}}[v_{dwell}^{U \to D}(m) + v_{dwell}^{U \to D}(n) + (N_{mn} - 2)\bar{v}_{scan}],$$

where $v_{weight}^{U \to D}$ is the weighted velocity in a downward direction through the singular cylindrical nanopore, $N_{mn}$ is the estimated number of monomers of the plurality of monomers, $v_{dwell}^{U \to D}(m)$ is the dwell velocity of the first protein tag in the downward direction through the singular cylindrical nanopore, $v_{dwell}^{U \to D}(n)$ is the dwell velocity of the subsequent protein tag in the downward direction through the singular cylindrical nanopore, and $\bar{v}_{scan}$ is the calculated average scanning velocity of the segment of double-stranded DNA.

5. The method of claim 4, further comprising a step of passing the segment of double-stranded DNA through the singular cylindrical nanopore in an opposing direction.

6. The method of claim 5, further comprising a step of calculating the weighted velocity of the segment of double-stranded DNA in an upward direction through the singular cylindrical nanopore using $$v_{weight}^{U \to D} = \frac{1}{N_{mn}}[v_{dwell}^{U \to D}(m) + v_{dwell}^{U \to D}(n) + (N_{mn} - 2)\bar{v}_{scan}].$$

7. The method of claim 1, further comprising a step of retaining at least a portion of the segment of double-stranded DNA within the singular cylindrical nanopore throughout each of the multiple scans.

8. The method of claim 1, further comprising a step of passing the segment of double-stranded DNA through the singular cylindrical nanopore in an opposing direction and repeating the steps of calculating the average scanning velocity, calculating the estimated distance between the first protein tag and the subsequent protein tag, calculating the estimated number of monomers of the plurality of monomers, calculating the weighted velocity of the segment of double-stranded DNA, and calculating the distance between the first protein tag and the subsequent protein tag.

9. The method of claim 8, further comprising a step of applying a bias voltage to the test chamber in a reverse direction prior to passing the segment of double-stranded DNA through the singular cylindrical nanopore in the opposing direction.

10. The method of claim 1, further comprising repeating the steps of calculating a distance between sequential protein tags for a plurality of protein tags within the segment of double-stranded DNA.

11. A method of calculating a distance between sequential protein tags within a segment of double-stranded DNA, the method comprising the steps of:
    applying a first voltage to a first side of a test chamber that defines a singular nanopore therethrough;
    based on the applied first voltage, passing the segment of double-stranded DNA through the first side of the singular nanopore defined by the test chamber, the segment of double-stranded DNA including a plurality of monomers, a first protein tag, and a subsequent protein tag, each of the plurality of monomers and each protein tag having an equal size, shape, and volume;
    applying a second voltage to a second side of the test chamber, the second side of the test chamber opposite the first side of the test chamber, such that a bias voltage applied to the test chamber reverses;
    based on the applied second voltage, passing the segment of double-stranded DNA through the second side of the singular nanopore in a direction toward the first side of the test chamber;

calculating an average scanning velocity of the segment of double-stranded DNA by dividing a length of the segment of double-stranded DNA by an average scanning time for the double-stranded DNA between the first side of the singular nanopore and the second side of the singular nanopore;

calculating an estimated distance between a first protein tag and a subsequent protein tag of the segment of double-stranded DNA by measuring, for the first protein tag and the subsequent protein tag, a dwell time and a dwell velocity based on an entry time into the singular nanopore and an exit time from the singular nanopore;

using the estimated distance between the first protein tag and the subsequent protein tag, calculating an estimated number of monomers of the plurality of monomers that are disposed between the first protein tag and the subsequent protein tag;

calculating a weighted velocity of the segment of double-stranded DNA using the dwell velocity for each of the first protein tag and the subsequent protein tag, the average scanning velocity of the segment of double-stranded DNA, and the estimated number of monomers; and calculating the distance between the first protein tag and the subsequent protein tag by multiplying the weighted velocity of the segment of double-stranded DNA by a time delay between the entry time of the first protein tag and the entry time of the subsequent protein tag.

12. The method of claim 11, wherein the test chamber includes a first longitudinal wall disposed at the first side opposite a second longitudinal wall disposed at the second side, with two opposing lateral walls joining the first longitudinal wall to the second longitudinal wall, such that the singular nanopore is formed between the two opposing longitudinal walls, wherein a central axis of the singular nanopore is parallel to each of the two opposing lateral walls.

13. The method of claim 11, wherein the singular nanopore is cylindrical in shape.

14. The method of claim 13, wherein the singular nanopore has an associated diameter of 2σ, where σ is a diameter of each of the plurality of monomers, the first protein tag, and the subsequent protein tag.

15. The method of claim 11, wherein the weighted velocity of the segment of double-stranded DNA is calculated using $$v_{weight}^{U \to D} = \frac{1}{N_{mn}} [v_{dwell}^{U \to D}(m) + v_{dwell}^{U \to D}(n) + (N_{mn} - 2)\bar{v}_{scan}],$$

where $v_{weight}^{U \to D}$ is the weighted velocity in a downward direction through the singular nanopore, $N_{mn}$ is the estimated number of monomers of the plurality of monomers, $v_{dwell}^{U \to D}(m)$ is the dwell velocity of the first protein tag in the downward direction through the singular nanopore, $v_{dwell}^{U \to D}(n)$ is the dwell velocity of the subsequent protein tag in the downward direction through the singular nanopore, and $\bar{v}_{scan}$ is the calculated average scanning velocity of the segment of double-stranded DNA.

16. The method of claim 11, further comprising a step of retaining at least a portion of the segment of double-stranded DNA within the singular nanopore throughout each of multiple scans.

17. The method of claim 11, further comprising repeating the steps of calculating a distance between sequential protein tags for a plurality of protein tags within the segment of double-stranded DNA.

18. A method of generating a barcode for a segment of double-stranded DNA by calculating a distance between sequential protein tags within the segment of double-stranded DNA, the method comprising the steps of:

passing the segment of double-stranded DNA through a singular cylindrical nanopore formed within a test chamber, the segment of double-stranded DNA including a plurality of monomers, a first protein tag, and a subsequent protein tag, each of the plurality of monomers and each protein tag having an equal size, shape, and volume;

calculating an average scanning velocity of the segment of double-stranded DNA by dividing a length of the segment of double-stranded DNA by an average scanning time for the double-stranded DNA taken for multiple scans;

for each of a plurality of protein tags on the segment of double-stranded DNA:

calculating an estimated distance between a first protein tag and a subsequent protein tag of the segment of double-stranded DNA by measuring, for the first protein tag and the subsequent protein tag, a dwell time and a dwell velocity based on an entry time into the singular cylindrical nanopore and an exit time from the singular cylindrical nanopore;

using the estimated distance between the first protein tag and the subsequent protein tag, calculating an estimated number of monomers of the plurality of monomers that are disposed between the first protein tag and the subsequent protein tag;

calculating a weighted velocity of the segment of double-stranded DNA using the dwell velocity for each of the first protein tag and the subsequent protein tag, the average scanning velocity of the segment of double-stranded DNA, and the estimated number of monomers; and calculating the distance between the first protein tag and the subsequent protein tag by multiplying the weighted velocity of the segment of double-stranded DNA by a time delay between the entry time of the first protein tag and the entry time of the subsequent protein tag; and generating the barcode for the segment of double-stranded DNA by arranging the plurality of protein tags of the segment of double-stranded DNA in sequential order.

19. The method of claim 18, wherein the singular cylindrical nanopore has an associated diameter of 2σ, where σ is a diameter of each of the plurality of monomers, the first protein tag, and the subsequent protein tag.

20. The method of claim 18, wherein the weighted velocity of the segment of double-stranded DNA is calculated using $$v_{weight}^{U \to D} = \frac{1}{N_{mn}} [v_{dwell}^{U \to D}(m) + v_{dwell}^{U \to D}(n) + (N_{mn} - 2)\bar{v}_{scan}],$$

where $v_{weight}^{U \to D}$ is the weighted velocity in a downward direction through the singular cylindrical nanopore, $N_{mn}$ is the estimated number of monomers of the plurality of monomers, $v_{dwell}^{U \to D}(m)$ is the dwell velocity of the first protein tag in the downward direction through the singular cylindrical nanopore, $v_{dwell}^{U \to D}(n)$ is the dwell velocity of the subsequent protein tag in the downward direction through the singular cylindrical nanopore, and $\bar{v}_{scan}$ is the calculated average scanning velocity of the segment of double-stranded DNA.

\* \* \* \* \*